United States Patent [19]
Murai et al.

[11] 3,966,728

[45] June 29, 1976

[54] BENZOGUANAMINE DERIVATIVES

[75] Inventors: Hiromu Murai; Katsuya Ohata; Yoshiaki Aoyagi; Fusao Ueda; Masahiko Kitano; Satoshi Takata; Shinichi Tada, all of Kyoto, Japan

[73] Assignee: Nippon Shinyaku Co., Ltd., Kyoto, Japan

[22] Filed: Jan. 27, 1975

[21] Appl. No.: 544,176

[30] Foreign Application Priority Data
Feb. 18, 1974 Japan................................ 49-19211
Feb. 18, 1974 Japan................................ 49-19212

[52] U.S. Cl............................. 260/249.9; 424/249
[51] Int. Cl.$^2$........................................ C07D 251/48
[58] Field of Search................................ 260/249.9

[56] References Cited

UNITED STATES PATENTS

| | | | |
|---|---|---|---|
| 3,471,490 | 10/1969 | Rafos et al....................... | 260/249.9 |
| 3,655,892 | 4/1972 | Bossinger et al................. | 260/249.9 |
| 3,716,536 | 2/1973 | Gund et al....................... | 260/249.9 |

*Primary Examiner*—John M. Ford

[57] ABSTRACT

A series of novel benzoguanamine derivatives possessing a high anti-peptic ulcer activity with low toxicity has been prepared by the reaction of the corresponding dihalogenobenzonitriles with dicyandiamide or by the reaction of the corresponding carboxylic acids or functional derivatives thereof with biguanide.

10 Claims, No Drawings

BENZOGUANAMINE DERIVATIVES

This invention relates to low toxicity benzoguanamine derivatives having valuable pharmacological activities, especially a high anti-peptic ulcer activity, which are represented by the following general formula

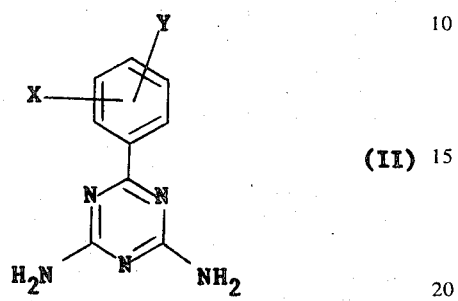

(II)

wherein X and Y stands for halogen atoms; excluding the compound in which X,Y = 3,4-dichloro.

In connection with derivatives of benzoguanamine, i.e., 2,4-diamino-6-phenyl-S-triazine, in addition to uses as additives to macromolecular materials and agricultural chemicals, it has heretofore been reported that some derivatives have diuretic, anti-inflammatory or anti-biotic activities, but it is not known that these derivatives have an anti-ulcerative activity or a similar pharmacological activity.

As a result of extensive and planned research on the synthesis of benzoguanimine derivatives and their pharmacological activities, we found that some benzoguanamine derivatives have a high anti-ulcerative activity. Accordingly, we synthesized a number of analogous compounds and made detailed comparative tests on them, and as a result it was found that dihalogenobenzoguanamines, namely 2,4-diamino-6-dihalogenophenyl-S-triazines, are generally highly active compounds. These dihalogenobenzoguanamines are novel compounds not disclosed in any known literature references except 3,4-dichlorobenzoguanamine. We succeeded in synthesizing all of these benzoguanamine derivatives in high yields according to the process detailed below.

Data of the anti-ulcerative activity (Shay rat) and the acute toxicity (mouse) obtained with respect to several typical instances of compounds included in the scope of this invention are shown in Table 1.

Table 1

| Compound Ex. No.) | % Inhibition of Ulcer Index | Dose (mg/Kg i.p.) | $LD_{50}$ (mg/Kg i.p.) |
|---|---|---|---|
| 1 | 100 %<br>49 % | 20<br>10 | about 1600 |
| 2 | 89 % | 20 | |
| 3 | 80 %<br>33 % | 20<br>10 | about 1000 |
| 4 | 78 % | 20 | about 500 |
| 5 | 100 % | 20 | about 850 |
| 6 | 86 %<br>35 % | 20<br>10 | above 1000 |
| 7 | 100 %<br>77 % | 20<br>10 | about 300 |
| 8 | 96 %<br>76 % | 20<br>10 | |
| 10 | 76 % | 20 | |
| 11 | 54 % | 20 | |
| 12 | 80 % | 20 | |

Novel benzoguanamine derivatives according to this invention can be prepared (1) by the reaction of the corresponding dihalogenobenzonitriles with dicyandiamide or (2) by the reaction of the corresponding carboxylic acids or functional derivatives thereof with biguanide. Details of such two methods are given below.

As to the first method, the compounds can be synthesized in high yields by reacting a dihalogenobenzonitrile compound of the formula

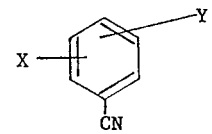

(where X and Y are the same or different halogens excluding a compound when (X,Y) is (3,4-dichloro)) with dicyandiamide. The reaction is preferably carried out in a lower alcohol such as methanol, ethanol, and butanol or in an organic polar solvent (inert) such as ethylene glycol, methylcellosolve, monoglyme, and diglyme and, preferably, in the presence of an alkali catalyst such as alkali hydroxide and sodium alcoholate. The resulting benzoguanamine derivatives of this invention can easily form salts with organic or inorganic acids, and salts with non-toxic acids include compounds having excellent properties as medicines.

As to the second method, the aimed compounds can be synthesized by the reaction of dihalobenzoic acid (excluding 3,5-dichlorobenzoic acid) or functional derivatives thereof (such as acid halides, acid amides, lower alkyl esters, or 2,x-dihalobenzoyl esters) with biguanide preferably in lower alcohol or organic polar inert solvent such as methylcellosolve and diglyme. In case it is necessary and desired, addition of equimolar amount of a base to the reaction mixture is preferred.

There are still other methods to manufacture the compounds of this invention. One of them is an amination of the corresponding dichloro compounds which may be represented by the following:

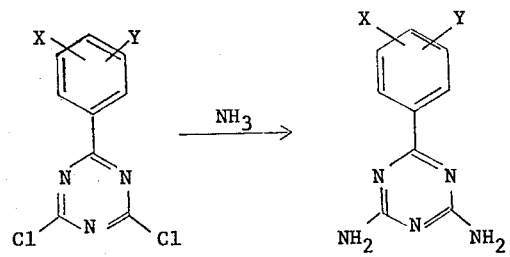

in which meanings of X and Y are the same as already defined.

In carrying out the above process, it is preferred that the starting dichloro compound is heated with concentrated ammonia water or with ammonia gas in a sealed tube at around 100°C for about 1 hour. The use of lower alcohol or dioxane or other hydrophilic solvent is preferred. Of course, the above statement is some of preferred embodiments of this amination process, so many more modifications are possible.

In order to save space, there is no detailed description of this amination process in the following examples but, of course, it should be understood that all compounds as referred to in the examples were prepared by the amination process. The yields were comparatively satisfactory.

Synthesis of some compounds included in the scope of this invention will now be illustrated in detail by reference to the following Examples.

EXAMPLE 1

(X, Y = 2,5-dichloro)

(1) 44 g of 2,5-dichlorobenzonitrile, 25.8 g of dicyandiamide and 2.5 g of potassium hydroxide were dissolved in 100 ml of methylcellosolve, and the mixture was heated and refluxed for 5 hours. The reaction mixture was cooled and 500 ml of water was added to the reaction mixture. The precipitated crystals were recovered by filtration and recrystallization from dioxane gave 58.5 g of the intended compound in the form of colorless crystals melting at 268° to 269°C. This compound will hereinafter be referred to as "compound A."

Elementary Analysis as $C_9H_7N_5Cl_2$: Calculated: C = 42.21%, H = 2.76%, N = 27.35%. Found: C = 42.06%, H = 2.57%, N = 27.31%.

The so obtained compound A was dissolved in dioxane and an equimolar amount of concentrated hydrochloric acid was added thereto. The mixture was dried to the solid under reduced pressure, and the residue was recrystallized from isopropanol to obtain a hydrochloride of the compound A having a melting point of 267° to 269°C. (decomposed at 180°C.).

Elementary Analysis as $C_9H_7N_5Cl_2 \cdot HCl$: Calculated: C = 36.94%, H = 2.75%, N = 23.94%. Found: C = 36.99%, H = 2.70%, N = 24.15%.

The compound A was dissolved in dioxane and an equimolar amount of hydrobromic acid was added thereto. The mixture was dried to the solid under reduced pressure and the residue was recrystallized from isopropanol to obtain a hydrobromide of the compound A having a melting point of 260° to 265°C.

Elementary Analysis as $C_9H_7N_5Cl_2 \cdot HBr$: Calculated: C = 32.07%, H = 2.39%, N = 20.78%. Found: C = 32.02%, H = 2.28%, N = 21.01%.

The compound A was dissolved in dioxane and methanesulfonic acid was added thereto in an amount of 2 moles per mole of the compound A. The mixture was dried to the solid under reduced pressure and the residue was recrystallized from acetone to obtain a methane-sulfonate of the compound A having a melting point of 160° to 162°C.

Elementary Analysis as $C_9H_7N_5Cl_2 \cdot 2CH_3SO_3H$: Calculated: C = 29.48%, H = 3.38%, N = 15.63%. Found: C = 29.20%, H = 3.50%, N = 15.58%.

Similarly prepared were the following acid addition salts of the compound A: perchlorate, m.p. 265°–275°C (decompn) (recrystd from isopropanol); hemisulfate, m.p. 255°–257°C (recrystd from methanol); monomethanesulfonate, m.p. 216°–220°C (recrystd from methanol); and maleate, m.p. 205°C (decompn) (recrystd from dioxane).

Another embodiments (2) to (5) of the synthesis of the compound A will now be described.

(2) 100 mg of 2,5-dichlorobenzonitrile, 100 mg of dicyandiamide and 100 mg of potassium hydroxide were dissolved in 5 ml of ethylene glycol, and the solution was heated at 110°C. for 6 hours. The reaction mixture was cooled and 10 ml of water was added thereto. Precipitated crystals were recovered by filtration and washed with ethanol to obtain 80 mg of a compound melting at 267° to 270°C., which was identified as the compound A by mixed examination and infrared absorption spectrum analysis.

(3) 100 mg of 2,5-dichlorobenzonitrile, 100 mg of dicyandiamide and 100 mg of sodium hydroxide were heated at 110°C. for 6 hours in 6 ml of ethylene glycol. The reaction mixture was cooled and then diluted with 10 ml of water. Precipitated crystals were recovered by filtration and washed with ethanol to obtain 50 mg of a compound melting at 270° to 272°C., which was identified as the compound A by mixed examination and infrared absorption spectrum analysis.

(4) 8.6 g of 2,5-dichlorobenzonitrile and 4.8 g of dicyandiamide were heated and refluxed under agitation for 4 hours in 150 ml of ethanol containing 1.3 g of metallic sodium dissolved therein. The reaction mixture was cooled and concentrated so that its volume was reduced to one-half. The concentrate was cooled, and precipitated crystals were recovered by filtration and recrystallized from ethanol to obtain 12.0 g of a compound having a melting point of 269° to 270°C., which was identified as the compound A by mixed examination and infrared absorption spectrum analysis.

(5) 0.86 g of 2,5-dichlorobenzonitrile and 0.48 g of dicyandiamide were added to 50 ml of methanol containing 0.25 g of metallic sodium dissolved therein, and the mixture was heated and refluxed under agitation for 12 hours. The reaction mixture was cooled, and insoluble crystals were recovered by filtration and recrystallized from ethanol to obtain 0.87 g of a compound melting at 267° to 269°C., which was identified as the compound A by mixed examination and infrared absorption spectrum analysis.

Still other embodiments to manufacture the compound A are as follows:

(1) 8.5 g of methyl 2,5-dichlorobenzoate and 6.4 g of biguanide were heated and refluxed for 3 hours in 100 ml of methylcellosolve. The reaction mixture liquid was evaporated to dryness under reduced pressure and water was added to the residue. Precipitated crystals were recovered by filtration and recrystallized from ethanol to obtain 3.09 g of the intended compound (hereinafter referred to as "compound A") in the form of colorless crystals having a melting point of 271° to 273°C.

Elementary Analysis as $C_9H_7N_5Cl_2$: Calculated: C = 42.21%, H = 2.75%, N = 27.34%. Found: C = 41.99%, H = 2.75%, N = 27.44%.

(2) 2.2 g of ethyl 2,5-dichlorobenzoate and 1.1 g of biguanide were heated and refluxed for 12 hours in 50 ml of ethanol. The reaction mixture liquid was dried to the solid under reduced pressure and water was added to the residue. Precipitated crystals were recovered by filtration and recrystallized from dioxane to obtain 1.26 g of a compound having a melting point of 268° to 269°C., which was identified as the compound A by mixed examination and infrared absorption spectrum analysis.

(3) 1.1 g of 2,5-dichlorobenzoic acid chloride was added dropwise to 20 ml of an ethanol solution containing 500 mg of biguanide and 500 mg of triethylamine, and the mixture was heated and refluxed for 6 hours. The reaction mixture liquid was dried to the solid under reduced pressure and ethanol was added to the residue. Precipitated crystals were recovered by filtration, washed with water and recrystallized from ethanol to obtain 0.72 g of a compound having a melting point of 267° to 270°C., which was identified as the compound A by mixed examination and infrared absorption spectrum.

(4) 0.95 g of 2,5-dichlorobenzamide and 0.5 g of biguanide were heated and refluxed in 20 ml of methylcellosolve for 16 hours. The reaction mixture liquid was dried to the solid under reduced pressure and water was added to the residue. Precipitated crystals were recovered by filtration and recrystallized from dioxane to obtain 0.75 g of a compound having a melting point of 267° to 269°C., which was identified as the compound A by mixed examination and infrared absorption spectrum analysis.

(5) 1.25 g of n-butyl 2,5-dichlorobenzoate and 500 mg of biguanide were heated and refluxed in 50 ml of n-butanol for 16 hours. The reaction mixture liquid was dried to the solid under reduced pressure, methanol was added to the residue and the mixture was allowed to stand still. Precipitated crystals were recovered by filtration and recrystallized from ethanol to obtain 0.46 g of a compound having a melting point of 269° to 271°C., which was identified as the compound A by mixed examination and infrared absorption spectrum analysis.

(6) 860 mg of 2,5-dichlorobenzoic anhydride (having a melting point of 111 to 112°C.) and 500 mg of biguanide were heated and refluxed in 20 ml of diglyme for 12 hours. The reaction mixture was cooled, 20 ml of water was added thereto, and the mixture was allowed to stand still in an ice chamber overnight. Precipitated crystals were recovered by filtration and recrystallized from ethanol to obtain 0.41 g of a compound having a melting point of 266° to 269°C., which was identified as the compound A by mixed examination and infrared absorption spectrum analysis.

(7) 0.95 g of 2,5-dichlorobenzoic acid and 500 mg of biguanide were heated and refluxed in 20 ml of diglyme for 12 hours. The reaction mixture was cooled and insoluble resinous substances were removed by filtration. Then, 50 ml of water was added to the filtrate and the mixture was allowed to stand still in an ice chamber overnight. Precipitated crystals were recovered by filtration and recrystallized from ethanol to obtain 0.3 g of a compound having a melting point of 265° to 269°C., which was identified as the compound A by mixed examination and infrared absorption spectrum analysis.

EXAMPLE 2

(X, Y = 2-fluoro-5-chloro)

0.6 g of 2-fluoro-5-chlorobenzonitrile, 0.5 g of dicyandiamide and 0.1 g of potassium hydroxide were heated at 150°C. under agitation for 5.5 hours in 20 ml of sec-octyl alcohol. The reaction mixture was cooled and water was added thereto. Precipitated crystals were recovered by filtration and washed with ethanol to obtain 0.36 g of the intended compound in the form of light-yellow crystals melting at 248° to 252°C.

Elementary Analysis as $C_9H_7N_5ClF$: Calculated: C = 45.10%, H = 2.94%, N = 29.23%, F = 7.93%. Found: C = 44.96%, H = 3.27%, N = 29.72%, F = 7.42%.

Another embodiment to manufacture the above compound is as follows:

3.2 g of methyl 2-fluoro-5-chlorobenzoate and 3.0 g of biguanide were heated and refluxed in 50 ml of ethanol containing 1.5 g of sodium methoxide dissolved therein for 6 hours. The reaction mixture liquid was dried to the solid under reduced pressure and water was added to the residue. Precipitated crystals were recovered by filtration and washed with water and ethanol to obtain 1.12 g of the intended compound in the form of colorless crystals melting at 249° to 255°C.

Elementary Analysis as $C_9H_7N_5ClF$: Calculated: C = 45.10%, H = 2.94%, N = 29.23%. Found: C = 44.89%, H = 3.20%, N = 29.50%.

EXAMPLE 3

(X, Y = 2-bromo-5-chloro)

6.0 g of 2-bromo-5-chlorobenzonitrile, 2.79 g of dicyandiamide and 1.5 g of potassium hydroxide were heated and refluxed in 15 ml of diglyme for 3 hours. The reaction mixture was cooled and 50 ml of water was added thereto. Precipitated crystals were recovered by filtration and recrystallized from methylcellosolve to obtain 2.4 g of the intended compound in the form of light-yellow crystals melting at 262° to 262.5°C.

Elementary Analysis as $C_9H_7N_5BrCl$: Calculated: C = 35.97%, H = 2.35%, N = 23.30%, Br = 26.59%, Cl = 11.80%. Found: C = 35.97%, H = 2.27%, N = 23.71%, Br = 26.08%, Cl = 12.04%.

EXAMPLE 4

(X, Y = 2-bromo-5-fluoro)

2.34 g of 2-bromo-5-fluorobenzonitrile, 2.94 g of dicyandiamide and 0.3 g of potassium hydroxide were dissolved in 30 ml of sec-butanol, and the solution was heated at 120°C. for 5 hours under agitation. The reaction mixture was cooled and water was added thereto. Precipitated crystals were recovered by filtration and washed with ethanol to obtain 1.5 g of the intended compound in the form of colorless crystals melting at 219° to 225°C.

Elementary Analysis as $C_9H_7N_5BrF$: Calculated: C = 38.05%, H = 2.48%, N = 24.65%. Found: C = 38.22%, H = 2.36%, N = 24.47%.

EXAMPLE 5

( X, Y = 2,5-dibromo )

3.5 g of 2,5-dibromobenzonitrile, 1.35 g of dicyandiamide and 1.0 g of potassium hydroxide were heated and refluxed for 4 hours in 20 ml of diglyme. The reaction mixture was cooled and 30 ml of water was added thereto. Precipitated crystals were recovered by filtration and recrystallized from dioxane to obtain 1.2 g of the intended compound in the form of colorless crystals melting at 272.5° to 274°C.

Elementary Analysis as $C_9H_7N_5Br_2$: Calculated: C = 31.33%, H = 2.05%, N = 20.30%, Br = 46.32%. Found: C = 31.53%, H = 1.92%, N = 20.45%, Br = 46.37%.

Another embodiment to manufacture the above compound is as follows:

1.2 g of methyl 2,5-dibromobenzoate and 0.6 g of biguanide were heated and refluxed in 10 ml of diglyme for 10 hours. The reaction mixture was cooled, diluted with 20 ml of water and allowed to stand still in an ice chamber overnight. Precipitated light-yellow powder was recovered by filtration and recrystallized from isopropanol to obtain 0.41 g of the intended compound in the form of colorless crystals melting at 271° to 273°C.

Elementary Analysis as $C_9H_7N_5Br_2$: Calculated: C = 31.33%, H = 2.05%, N = 20.30%. Found: C = 31.08%, H = 2.29%, N = 20.11%.

EXAMPLE 6

(X, Y = 2-chloro-5-bromo)

6.0 g of 2-chloro-5-bromobenzonitrile, 2.79 g of dicyandiamide and 1.0 g of potassium hydroxide were heated and refluxed in 15 ml of diglyme for 3 hours. The reaction mixture was cooled and 50 ml of water was added thereto. Precipitated crystals were recovered by filtration and recrystallized from a dioxane-ethanol mixture to obtain 2.3 g of the intended compound in the form of light-yellow crystals melting at 280° to 281.5°C.

Elementary Analysis as $C_9H_7N_5BrCl$: Calculated: C = 35.97%, H = 2.35%, N = 23.30%, Br = 26.59%, Cl = 11.80%. Found C = 36.01%, H = 2.34%, N = 23.19%, Br = 26.86%, Cl = 11.37%.

EXAMPLE 7

(X, Y = 2,4-dichloro)

9.0 g of 2,4-dichlorobenzonitrile, 5.5 g of dicyandiamide and 1.0 g of potassium hydroxide were heated and refluxed for 5 hours in 20 ml of methylcellosolve. The reaction mixture was cooled and 50 ml of water was added thereto. Precipitated crystals were recovered by filtration and recrystallized from acetone to obtain 5.9 g of the intended compound in the form of colorless crystals melting at 204° to 206°C.

Elementary Analysis as $C_9H_7N_5Cl_2$: Calculated: C = 42.20%, H = 2.76%, N = 27.35%. Found: C = 42.41%, H = 2.70%, N = 27.02%.

The so obtained compound was dissolved in dioxane and an equimolar amount of hydrochloric acid was added to the solution. The mixture was dried to the solid under reduced pressure and the residue was recrystallized from isopropanol to obtain a hydrochloride of the above compound having a melting point of 200° to 205°C. (decomposed at 180°C.).

Elementary Analysis as $C_9H_7N_5Cl_2 \cdot HCl$: Calculated: C = 36.94%, H = 2.75%, N = 23.94%. Found: C = 36.68%, H = 2.77%, N = 24.27%.

Further, the above compound was dissolved in dioxane and an equimolar amount of p-toluene-sulfonic acid was added to the solution. The mixture was dried to the solid under reduced pressure and the residue was recrystallized from acetone to obtain a p-toluenesulfonate of the above compound having a melting point of 224° to 227°C.

Elementary Analysis as $C_9H_7N_5Cl_2 \cdot CH_3C_6H_4SO_3H$: Calculated: C = 44.87%, H = 3.53%, N = 16.35%. Found: C = 44.62%, H = 3.62%, N = 16.34%.

Another embodiment to manufacture the above compound is as follows:

2.1 g of methyl 2,4-dichlorobenzoate and 1.1 g of biguanide were heated and refluxed in 50 ml of methanol containing 0.25 g of metallic sodium dissolved therein for 4 hours. The reaction mixture liquid was dried to the solid under reduced pressure and water was added to the residue. Precipitated crystals were recovered by filtration and recrystallized from acetone to obtain 2.2 g of the intended compound having a melting point of 206° to 207°C.

Elementary Analysis as $C_9H_7N_5Cl_2$: Calculated: C = 42.21%, H = 2.76%, N = 27.35. Found: C = 42.12%, H = 2.65%, N = 27.34.

Still another embodiment is as follows:

2.4 g of n-propyl 2,4-dichlorobenzoate and 1.1 g of biguanide were heated at 140°C. for 6 hours in 10 ml of ethylene glycol. The reaction mixture was cooled, 30 ml of water was added thereto, and the mixture was allowed to stand still in an ice chamber overnight. Precipitated crystals were recovered by filtration and recrystallized from acetone to obtain 1.4 g of a compound in the form of colorless crystals melting at 202° to 204°C.

EXAMPLE 8

(X, Y = 2-bromo-4-chloro)

1.0 g of 2-bromo-4-chlorobenzonitrile, 0.52 g of dicyandiamide and 0.1 g of potassium hydroxide were heated at 110° to 120°C. for 5 hours in 5 ml of diglyme. The reaction mixture was cooled and 10 ml of water was added thereto. Precipitated crystals were recovered by filtration and recrystallized from ethanol to obtain 1.27 g of the intended compound in the form of colorless crystals melting at 215° to 216°C.

Elementary Analysis as $C_9H_7N_5BrCl$: Calculated: C = 35.96%, H = 2.35%, N = 23.30%. Found: C = 35.69%, H = 2.16%, N = 23.07%.

EXAMPLE 9

(X, Y = 2-fluoro-4-chloro)

0.4 g of 2-fluoro-4-chlorobenzonitrile, 0.33 g of dicyandiamide and 0.1 g of potassium hydroxide were heated and refluxed in 2 ml of diglyme for 5 hours. The reaction mixture was cooled and 3 ml of water was added thereto. Precipitated crystals were recovered by filtration and recrystallized from acetone to obtain 165 mg of the intended compound in the form of colorless crystals having a melting point of 307°C. (decomposition).

Elementary Analysis as $C_9H_7N_5ClF$: Calculated: C = 45.10%, H = 2.94%, N = 29.23%. Found: C = 45.40%, H = 2.73%, N = 28.90%.

EXAMPLE 10

(X, Y = 2,3-dichloro)

0.8 g of 2,3-dichlorobenzonitrile, 1.25 g of dicyandiamide and 0.4 g of potassium hydroxide were heated and refluxed in 20 ml of methylcellosolve for 2 hours. The reaction mixture was cooled and 100 ml of water was added thereto. Precipitated crystals were recovered by filtration and recrystallized from isopropanol to obtain 0.5 g of the intended compound in the form of colorless crystals melting at 240° to 242°C.

Elementary Analysis as $C_9H_7N_5Cl_2$: Calculated: C = 42.20%, H = 2.76%, N = 27.35%. Found: C = 42.38%, H = 2.53%, N = 26.93%.

EXAMPLE 11

(X, Y = 2,6-dichloro)

8.6 g of 2,6-dichlorobenzonitrile, 5.3 g of dicyandiamide and 3.6 g of potassium hydroxide were heated and refluxed in 100 ml of ethylcellosolve for 4 hours. The reaction mixture was cooled and 300 ml of water added thereto. Precipitated crystals were recovered by filtration and recrystallized from dioxane to obtain 1.18 g of the intended compound in the form of colorless crystals melting at 261° to 265°C.

Elementary Analysis as $C_9H_7N_5Cl_2$: Calculated: C = 42.20%, H = 2.76%, N = 27.35%. Found: C = 42.48%, H = 2.55%, N = 27.65%.

EXAMPLE 12

(X, Y = 3,5-dichloro)

1.93 g of 3,5-dichlorobenzonitrile, 1.18 g of dicyandiamide and 0.98 g of potassium hydroxide were heated and refluxed in 35 ml of methylcellosolve for 5 hours. The reaction mixture was cooled and diluted with 100 ml of water. Precipitated crystals were recovered by filtration and recrystallized from dioxane to obtain 1.1 g of the intended compound in the form of colorless crystals having a melting point higher than 300°C.

Elementary Analysis as $C_9H_7N_5Cl_2$: Calculated: C = 42.20%, H = 2.76%, N = 27.35%. Found: C = 42.56%, H = 2.49%, N = 27.50%.

EXAMPLE 13

(X, Y = 2-chloro-5-fluoro)

1.0 g of 2-chloro-5-fluorobenzonitrile and 1.1 g of dicyandiamide were dissolved in 10 ml of sec-octyl alcohol containing 0.1 g of potassium hydroxide, and the solution was heated at 150°C. for 4 hours. The reaction mixture was cooled and diluted with 10 ml of water. Precipitated crystals were recovered by filtration and recrystallized from ethanol to obtain 0.4 g of the intended compound having a melting point of 215° to 216°C.

Elementary Analysis as $C_9H_7N_5ClF$: Calculated: C = 45.10%, H = 2.94%, N = 29.23%. Found: C = 45.01%, H = 2.66%, N = 29.50%.

EXAMPLE 14

(X, Y = 3-chloro-4-bromo)

1.3 g of 3-chloro-4-bromobenzonitrile (having a melting point of 79° to 80°C.) and 0.8 g of dicyandiamide were dissolved in 10 ml of methylcellosolve containing 0.2 g of sodium hydroxide, and the solution was heated at 110°C. for 4 hours. The reaction mixture was cooled and 10 ml of water was added thereto. Precipitated crystals were recovered by filtration and recrystallized from ethanol to obtain 0.8 g of the intended compound having a melting point of 269° to 272°C.

Elementary Analysis as $C_9H_7N_5BrCl$: Calculated: C = 35.96%, H = 2.35%, N = 23.30%, Br = 26.59%. Found: C = 36.37%, H = 2.37%, N = 22.57%, Br = 26.02%.

EXAMPLE 15

(X, Y = 2-fluoro-5-bromo)

1.65 g of methyl 2-fluoro-5-bromobenzoate and 1.5 g of biguanide were heated and refluxed in 100 ml of methanol for 8 hours. The reaction mixture liquid was dried to the solid under reduced pressure and 100 ml of water was added to the residue. Precipitated crystals were recovered by filtration and recrystallized from isopropanol to obtain 0.9 g of the intended compound in the form of colorless crystals having a melting point of 268° to 272°C.

Elementary Analysis as $C_9H_7N_5BrF$: Calculated: C = 38.05%, H = 2.48%, N = 24.65%. Found: C = 37.77%, H = 2.50%, N = 24.35%.

EXAMPLE 16

(X, Y = 2,5-difluoro)

0.3 g of ethyl 2,5-difluorobenzoate and 0.3 g of biguanide were heated and refluxed in 50 ml of methanol for 19 hours. Methanol was distilled under reduced pressure and water was added to the residue. Precipitated crystals were recovered by filtration and recrystallized from ethanol to obtain 0.15 g of the intended compound having a melting point of 241° to 243°C.

Elementary Analysis as $C_9H_7N_5F_2$: Calculated: C = 48.43%, H = 3.16%, N = 31.38%. Found: C = 48.41%, H = 3.35%, N = 31.69%.

EXAMPLE 17

(X, Y = 2-bromo-4-chloro)

1.1 g of methyl 2-bromo-4-chlorobenzoate and 0.9 g of biguanide were heated and refluxed in 20 ml of n-propanol for 16 hours. The reaction mixture was cooled and diluted with 20 ml of water. A precipitated brown substance was removed by filtration, and the filtrate was allowed to stand still in an ice chamber overnight. Precipitated yellow powder was recovered by filtration and recrystallized from ethanol to obtain 0.66 g of the intended compound having a melting point of 215° to 217°C.

Elementary Analysis as $C_9H_7N_5BrCl$: Calculated: C = 35.96%, H = 2.35%, N = 23.30%. Found: C = 35.86%, H = 2.11%, N = 23.61%.

EXAMPLE 18

(X, Y = 2-chloro-5-fluoro)

1.0 g of ethyl 2-chloro-5-fluorobenzoate and 1.0 g of biguanide were heated and refluxed in 50 ml of ethanol for 8 hours. The reaction mixture liquid was dried to the solid under reduced pressure and water was added to the residue. Precipitated crystals were recovered by filtration, washed with water and recrystallized from ethanol to obtain 0.4 g of the intended compound having a melting point of 214° to 216°C.

Elementary Analysis as $C_9H_7N_5ClF$: Calculated: C = 45.10%, H = 2.94%, N = 29.23%. Found: C = 45.31%, H = 2.90%, N = 28.92%.

What is claimed is:

1. A benzoguanamine derivative of the formula:

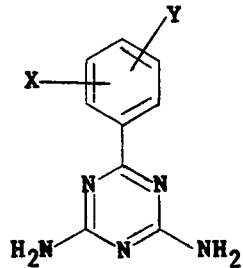

in which X and Y are the same or different halogens in the 2- and 5-positions.

2. The compound of claim 1 in which X,Y is 2,5-dichloro.

3. The compound of claim 1 in which X,Y is 2-fluoro-5-chloro.

4. The compound of claim 1 in which X,Y is 2-bromo-5-chloro.

5. The compound of claim 1 in which X,Y is 2-bromo-5-fluoro.

6. The compound of claim 1 in which X,Y is 2,5-dibromo.

7. The compound of claim 1 in which X,Y is 2-chloro-5-bromo.

8. The compound of claim 1 in which X,Y is 2-chloro-5-fluoro.

9. The compound of claim 1 in which X,Y is 2-fluoro-5-bromo.

10. The compound in claim 1 in which X,y is 2,5-difluoro.

* * * * *